United States Patent
Bakovic et al.

(10) Patent No.: US 6,777,216 B2
(45) Date of Patent: Aug. 17, 2004

(54) ETHANOLAMINEPHOSPHATE CYTIDYLYTRANSFERASE GENE AND PROMOTER

(75) Inventors: Marica Bakovic, Guelph (CA); Arkadi Poloumienko, Guelph (CA)

(73) Assignee: University of Guelph, Guelph (CA)

( * ) Notice: Subject to any disclaimer, the term of this patent is extended or adjusted under 35 U.S.C. 154(b) by 135 days.

(21) Appl. No.: 10/101,957

(22) Filed: Mar. 21, 2002

(65) Prior Publication Data

US 2003/0194795 A1 Oct. 16, 2003

(51) Int. Cl.$^7$ .............................. C12N 9/10; C07H 21/04
(52) U.S. Cl. ...................... 435/193; 536/23.2; 536/24.1
(58) Field of Search ............................. 435/193, 252.3, 435/320.1; 536/23.2, 24.1

(56) References Cited

PUBLICATIONS

Bazzi et al. (1991) Biochemistry 31, 1125–1134.
Bogdanov et al. (1999) J. Biol. Chem. 274, 12339–12345.
Engelmann et al. (1998) J. Biol. Chem. 273, 27800–27808.
Gilbert et al. (2000) J. Biol. Chem. 270, 18500–18505.
Smirnov et al. (1995) J. Clin. Invest. 95, 309–316.
Mileykovskaya et al. (1998) J. Bacteriol. 180, 4252–4257.
Emoto et al. (1996) Proc. Natl. Acad. Sci. 93, 12867–12872.
Emoto et al. (1997) Exp. Cell Res. 232, 430–434.
Ellens et al. (1989) Biochem. 28, 3692–3703.
Aoki et al. (1994) J. Biochem. 116, 291–297.
Menon et al. J. Biol. Chem., 267, 15277–15280.
Menon et al. (1993) EMBO J., 12, 1907–1914.
Kamitani et al.(1992) J. Biol. Chem., 267, 24611–24619.
Hong et al. (1999) J. Biol. Chem., 274, 35099–35106.
Van den Bosch et al.(1992) Annu. Rev. Biochem. 61, 157–197.
Jira et al. (1996) Chem. Phys. Lipids, 79, 95–100.
Falibrook et al, (1999) Brain Res. 834, 207–210.
Xu et al. (1991) J. Biol. Chem., 266, 2143–2150.
Snyder (1985) In Biochemistry of Lipid and Membranes (Vance, D.E. and Vance, J.E. Eds.) pp 271–298, Benjamin Commings Publishing Co., Menlo Park, CA.
Porter et al. (1990) J. Biol. Chem. 265, 414–422.
Lee (1998) Biochim. Biophys. Acta, 1394, 129–145.
Datta et al. (1984) New Engl. J. Med., 311, 1080–1083.
Schrakamp et al. (1985) Biochim. Biophys. Acta, 833, 170–174.
Ravandi et al. (1999) J. Biol. Chem., 274, 16494–16500.
Ishidate et al.(1985) Biochim. Biophys. Acta. 833, 1–8.
Tadokoro (1985) Biochim. Biophys. Acta. 835, 501–513.
Uchida et al. (1992) J. Bio. Chem. 267, 10156–10162.
Aoyama et al. (1992) Biochim. Biophys. Acta. 1390, 1–7.
Aoyama (2000) J. Lipid Res. 41, 452–464.
Vermeulen et al. (1997) Advances in Lipobiology. 2, 287–322.
Polokoff et al. (1981) J. Biol. Chem. 256, 7687–7690.
Vance et al.(1992) J. Biol. Chem. 263, 5898–5909.
Hjelmstad et al. (1991) J. Biol. Chem. 266, 5096–5103.
Henneberry et al. C.R. (1999) Biochem. J. 339, 291–298.
Tiburg et al. (1987) Biochim. Biophys. Acta. 922, 184–190.
Vermeulen et al. (1994) Biochim. Biophys. Acta. 1211, 343–349.
Van Hellemond et al. (1994) J. Biol. Chem. 269, 15415–15418.
Vermeulen et al. (1993) J. Biol. Chem. 268, 7458–7464.
Min–Seok et al, (1996) J. Biochem. 120, 1040–1047.
Nakashima et al. (1997) J. Biol. Chem. 272, 9567–9572.
Bladergroen et al. (1999) Biochem. J. 343, 107–114.
Bork et al.(1995) Proteins 22, 259–266.
Bladergoen et al. (1999) Biochem. J., 343, 107–114.
Sugumoto et al.(2001) J. Biol. Chem. 276, 12338–12344.
Mallampalli et al. (2000) J. Biol. Chem. 275, 9699–9708.
Lykidis et al. (1999) J. Biol. Chem. 274, 26992–27001.
Lykidis et al. (1998) J. Biol. Chem. 273, 14022–14029.
Bladergroen et al. (1997) Biochim. Biophys. Acta. 1348, 91–99.
Kikuch et al. (1999) Comp. Biochem. Physiol. 124B, 1–6.
Xu et al. (1991) J. Biol. Chem. 266, 2143–2150.
Lee et al.(1998) Biochim. Biophys. Acta. 1398, 129–145.
Mount et al. (1982) Nucleic Acid Res., 10, 459–472.
Lanie et al. (1997) Int. J. Biochem. Cell Biol. 29, 1313–1323.
Bakovic et al. (2000) J. Lipid Res. 41, 583–594.

*Primary Examiner*—Tekchand Saidha
(74) *Attorney, Agent, or Firm*—David L. Conn; Borden Ladner Gervais LLP

(57) ABSTRACT

The invention provides a gene encoding a protein having ethanolaminephosphate cytidylyltransferase activity, and a promoter of an ethanolaminephosphate cytidylyltransferase gene. Nucleotide sequences according to SEQ ID NO:1 and SEQ ID NO:2 relate to the gene and the promoter, respectively.

3 Claims, 8 Drawing Sheets

```
Consensus         ................................................. 50
BC003473  mET     MIRNGHGAAS..AAGLKGPGGQ.R..VRVNDDGC.YDMVHYGHSN.QIRQARAMGD  50
          rET     MIRNGHGAAS..AAGLKGPGDQ.RIVRVWCDGC.YDMVHYGHSN.QIRQARAMGD  50
          hET     MIRNGHGAEG..AAGLKGPGEQ.RIVRVWCDGG.YDMVHYGHSN.QIRQARAMGD  50
                  MIRNGRGAAG..GAFQPGPGGR.RAVRVWCDEC.YDMVHYGESN.QIRQARAMGD  50

BC003473  mET     YLIVGVHDE.EIAKHRGPPY.FTQEERYKMV.QAIKWVDEVV.PAMPYVHELE  100
          rET     YLIVGVHDE.EIAKHRGPPV.FNQMRYKYMV.QAIKWVDEVV.PSDxxxxxx   100
          hET     YLIVGVHDE.EIAKWKGPPV.FTQEERYKMV.QAIKWVDEVA.AAPKV....   100
                  VLIVGVHTDF.EIAKHKGRPV.FTQEERYKMV.QAIKWVDEVV.PAAxxxxxx  100

BC000347  mET     TLDx.N.D..VH.ND..ITV..GRD.YEEVK.QAGR..EC              150
          rET     xLDKHNXDWS.VHCNDVVLTV.YCRESYEEYK..................    139
          hET     TLMTSRXQXM.AEIPTRKKSR.LGGTESANAP...................   140
                  xLDKYNCBFC.VRGNDILLTV.DGRDTYEEVR...................   150
```

FIG. 2

```
           +1
            ↓
D84307     attgcgggcg gcggcgttcg gagtcgccgg gagctgccag gctgtccgcg ccgccgctgc   60
hET-C5.3   ------------------gtcgccgg gagctgccag gctgtccgcg ccgccgctgc
hET-C2.3   ----------------------------------------------------------
hET-C1.1   ----------------------------------------------------------

↓
D84307     ggggccatga tccggaacgg gcgcggggct gcaggcggcg cagagcagcc gggcccggg    120
hET-C5.3   ggggccatga tccggaacgg gcgcggggct gcaggcggcg cagagcagcc gggcccgggg
hET-C2.3   ---------------------------------------------------------gggcccgggg
hET-C1.1   -------------------------------------------------------ccgggcccgggg D84307     ggcaggcgcg ccgtgagggt gtggtgcgat ggctgctatg acatggtgca ttacggccac   180
hET-C5.3   ggcaggcgcg ccgtgagggt gtggtgcgat ggctgctatg acatggtgca ttacggccac
hET-C2.3   ggcaggcgcg ccgtgagggt gtggtgcgat ggctgctatg acatggtgca ttacggccac
hET-C1.1   ggcaggcgcg ccgtgagggt gtggtgcgat ggctgctatg acatggtgca ttacggccac D84307     tccaaccagc tgcgccaggc acgggccatg ggtgactacc tcatcgtagg cgtgcacacc   240
hET-C5.3   tccaaccagc tgcgccaggc acgggccatg ggtgactacc tcatcgtagg cgtgcacacc
hET-C2.3   tccaaccagc tgcgccaggc acgggccatg ggtgactacc tcatcgtagg cgtgcacacc
hET-C1.1   tccaaccagc tgcgccaggc acgggccatg ggtgactacc tcatcgtagg cgtgcacacc D84307     gatgaggaga tcgccaagca caaggggccc ccggtgttca ctcaggagga gagatacaag   300
hET-C5.3   gatgaggaga tcgccaagca caaggggccc ccggtgttca ctcaggagga gagatacaag
hET-C2.3   gatgaggaga tcgccaagca caaggggccc ccggtgttca ctcaggagga gagatacaag
hET-C1.1   gatgaggaga tcgccaagca caaggggccc ccggtgttca ctcaggagga gagatacaag D84307     atggtgcagg ccatcaaatg ggtggacgag gtg                                 333
hET-C5.3   atggtgcagg ccatcaaatg ggtggacgag gtg
hET-C2.3   atggtgcagg ccatcaaatg ggtggacgag gtg
hET-C1.1   atggtgcagg ccatcaaatg ggtggacgag gtg
                         _____/
                                I2RP
```

FIG. 7

```
CCCCGAGTGG TCGGCCCGGG CTCCCCGGGC TCAGGTCTGC CGCCT GGCAGCTCGG TCGTG    -448
                                                  AP4

GCTTAAAACT CCCTTGGTTG GACAGGG GACAACTGTA GAT TATTGTGCCA AAAAATAAGA   -388
                              MYOD

AAAAAAACTC CCCTGGTTGG GACAGCGCCCCGTGGAG GTT CCCGGAGGTG GCGGCG GTGG   -328
                      AP4      AP2                            NFKappaB→

GACGGTCCCCACGCCG CACT GCCCC GCCAGCCGAGCGCCAGG TG TGGGCGGTGCG GAGAG   -268
       AP2                  AP4           MYOD       Sp1

GCCAGGTGTGG GTC GGGGGGCGGGGC TCGGAAAGCGCGGC ACACGC CATTGGCTGTGCGT    -208
   MYOD        Sp1                                  NF1→

TTGG AGGGGGCGGGACT CTG TCAGGGGCTC ACGCCATTGG CCGTGCGCGG AGGTGCGGTG   -148
     Sp1

GGGCGCGGCC TTC GGGGGGTGGGGCTCGGGGCGGAGGGCGGGAGGCGGGGCGGGGGA AGC      -88
               Sp1          Sp1       Sp1       Sp1

GGGGGCTGGGCT CGGGCCGA GCGCCAC CCAT TGGCCGTG CGCAGCGGGT GAGGCCCGCG    -28
   Sp1                       CAAT BOX       AP4

TGACGGCCGC TGAGCGTG CGCTGGCGGGGCGGGCGGCGG CGCTCGGAGTCGCCGGGAGCT      +32
                    Sp1  Sp1  Sp1                ↑

GCCAGGCTGC TCCGCGCGCC *GCTGCGGGGC CATGATCCGG AACGGGCGCG GGGCTGCAGG*  +92
```

FIG. 8

ETHANOLAMINEPHOSPHATE CYTIDYLYTRANSFERASE GENE AND PROMOTER

FIELD OF THE INVENTION

The present invention relates generally to the fields of genes and promoters. More particularly, the present invention relates to an isolated gene and promoter of the enzyme ethanolaminephosphate cytidylyltransferase.

BACKGROUND OF THE INVENTION

Phosphatidylethanolamine (PE) is an abundant lipid in both eukaryotic and prokaryotic cells. PE is situated primarily on the inner leaflet of the cell membrane where it interacts with inner-membrane proteins (1) or acts as a molecular chaperone and assists in proper protein folding (2). PE also plays an important role in physiological processes such as blood coagulation, platelet activation, cell signalling, membrane fusion, cell cycle progression, cell division, and apoptosis (3–9). Transfer of PE from lipoproteins to platelets induces their activation (3) and PE induces high-affinity binding sites for factor VIII and stimulates its pro-coagulant activity (4). PE is also involved in the thrombotic activity found in some cases of lupus where it further inhibits activated protein C (5). PE is a direct precursor of other lipids and provides ethanolamine moiety for anandamide (a physiological ligand for the cannabioid receptors) and glycosylphospatidylinositol (GPI) membrane anchors for a diverse group of proteins known as proteoglycans.

Distribution of PE in membranes plays a pivotal role during cytokinesis (7). Prior to late telophase, PE becomes exposed on the cell surface at the cleavage furrow, where it regulates the movement of the actin contractile ring and plasma membrane (7). Interestingly, the surface trapping of PE causes cell arrest (10), and the appearance of PE (together with PS) on the cell surface is an early hallmark of apoptosis (8). Products of PE metabolism, fatty acids, diacylglycerols and phosphatidic acid serve a critical role as second messengers in various signalling pathways and PE is an immediate donor of phosphoethanolamine residue linking glycosylphosphatydylinositol (GPI) anchor to proteins (11–14). There exist specialized forms of PE such as plasmalogens and derivatives such as natural cannabinoid anandamide and glycosylated PE (15–17). Plasmalogens play a role in the prevention of oxidation of lipoproteins (16) and constitute a significant portion of total PE in many tissues (18,19). However, despite their relative abundance, the principal biological function of plasmalogens is not firmly established and the understanding of the regulation of their production is surprisingly limited. Their production is severely impaired in the peroxisomal disorders such as Zellweger syndrome, Refsum disease (11) and neurological disorders (21–23). Glycosylated PE is abundant in lipoproteins of diabetics and has been implicated in the promotion of atherosclerosis in those individuals (24).

There are several pathways for the biosynthesis of PE, certain of which form PE from the alteration of other lipids. These include the decarboxylation of phosphatidylserine (PS) by a PS decarboxylase (PSD) and the base-exchange reaction with PS by a PS synthase (PSS) or phosphatydylcholine (PC). The third pathway, the CDP-ethanolamine pathway or Kenedy pathway, synthesizes PE de novo from ethanolamine and diacylglycerols (DAGs). The CDP-ethanolamine pathway includes three enzymatic steps consisting of the phosphorylation of ethanolamine (Etn), the formation of CDP-ethanolamine and pyrophosphate from phosphoethanolamine (P-Etn), and the final formation of PE from the transfer of phosphoethanolamine from CDP-ethanolamine (CDP-Etn) to diacylglycerol (DAG). These three steps are catalyzed by the enzymes ethanolamine kinase (EK), CTP:phosphoethanolamine cytidylyltransferase (ET), and ethanolaminephosphotransferase (EPT), respectively as shown in FIG. 1.

Little is known about genomic regulation of the biosynthesis of phospholipids. Several control points for the regulation of PE biosynthesis have been suggested. The reaction catalyzed by CTP: ethanolaminephosphate cytidilyltransferase (ET) has been suggested as a major regulatory step in the PE biosynthetic pathway. Considerable effort has been focused on the regulation of genes that encode enzymes in the fatty acid and cholesterol synthesis pathways. Promoters of these genes contain sterol-regulatory elements and are regulated by cholesterol-responsive transcription factors, sterol regulatory element binding proteins (SREBPs). However, lipogenic enzymes are mainly regulated by dietary carbohydrates, and their promoters contain insulin-response elements. The role for SREBPs in the regulation of fatty acid genes has been ascribed as means for cholesterol regulation of membrane phospholipids, typified in phosphatydyl choline production but direct regulation with cholesterol has also been suggested.

Studies on the regulation of genes that encode phospholipid biosynthetic enzymes have lagged behind that of other classes of lipogenic genes, primarily because most phospholipid-biosynthetic enzymes are difficult to isolate owing to their association with membranes. No evidence for direct transcriptional control of phospholipid genes with cholesterol, fatty acids or carbohydrates has yet been produced, but it is possible that these factors may have influence. Future experimentation with a combination of different transgenic models may determine specific genetic links for carbohydrate, cholesterol and phospholipid metabolism. Furthermore, additional links with regulators of lipid metabolism, including the peroxisome proliferator activated receptors (PPARs) and lipoproteins may be found. PPARs are activated by a diverse group of pharmacological ligands, the peroxisome proliferators (e.g., fibrates, troglitazone), which are well known drugs for regulating lipoprotein levels and very important for prevention of atherosclerosis.

Ethanolamine kinase (EK) exists in several isoforms (20,25,26) having both EK and choline kinase (CK) activities. The isolation of two rat cDNA clones for CK/EK has allowed for the characterization of two separate rat genes (27, 28) and two mouse gene products (29). Unlike CK/EK, EPT is responsible for production of PE by transferring phosphoethanolamine from CDP-ethanolamine to DAG (30) and a separate enzyme, cholinephophotransferase (CPT), is responsible for this reaction in the CDP-choline pathway. EPT and CPT are encoded by two separate genes (31,32). The EPT gene was cloned by complementation of an EPT yeast mutant with a yeast genomic library (33). Subsequently, the human cDNA for EPT has been isolated (34). Interestingly, the human EPT protein has broad substrate specificity, and has the ability to form both choline and ethanolamine lipids (34).

CTP: phosphoethanolamine cytidylyltransferase (ET) is one of the most substrate-specific and the most regulatory enzyme in the CDP-ethanolamine pathway (35). Only rat ET protein has been successfully purified and its biochemical properties clearly established (36–38). The rat protein is considered soluble but could localize between the cisternae of the rough ER and the cytosolic space suggesting some associations with membranes (37). Unlike CK/EK and EPT, rat ET only has activity towards ethanolaminephosphate and does not show any affinity for cholinephosphate (38). These findings strongly agree with genetic evidence indicating that ET and CTP: phosphocholine cytidylyltransferase (CT) cDNAs are produced by two different genes (39, 40). ET cDNAs from yeast, human, and rat have been functionally characterized and showed a high degree of homology between sequences (39–41). Neither the mouse ET cDNA nor any ET gene has yet been characterized.

An EST (GenBank™ Accession No. BC003473) encoding 1855 bp of mRNA for the full-length mouse ET was identified, and is highly homologous to rat and human cDNAs, particularly in the proximity of the translation start codon ATG as shown in FIG. 2. Computer analysis suggests that ET protein possesses a recognition motif MIRNG and two catalytic domains with large internal repetitive sequences in its N-and C-terminal halves; both parts of the sequence contain the CTP-binding motif HXGH (41), which is conserved in the entire cytidylyltransferase superfamily (42). CT does not contain the MIRNG motif, does not have two similar halves, and possesses only single HXGH motif (39, 40).

Even though ET is a critical enzyme required for the de novo synthesis of PE, no gene has been characterized and little is known about the regulation of this enzyme's expression. Recent evidence (43) indicates that rat ET mRNA and protein level increase during liver development; a higher change in mRNA than protein was visible, suggesting that combined transcriptional and translational events are may be involved in the regulation of ET activity. It would be advantageous to fully elucidate the regulation of the ET gene product.

Little effort has been given towards the study of ET regulation at the genetic level. This is due to the fact that it was often assumed that ET is similar to CTP: phosphocholine cytidylyltransferase (CT), the major regulatory enzyme in the CDP-choline pathway for the biosynthesis of phosphatidylcholine (PC) (44–48). It was not until recently that it was speculated that ET was regulated in a different manner than CT (49) and that PE's importance may not lie in the fact that it only resides in cell membranes but rather that it can be found in other forms that could play vital roles in proper cell functioning. Further examples of this are PE plasmalogens, which comprise a large portion of total cellular PE (50) and may play an important role in proper functioning of the brain and heart (51). It would be of great interest to fully understand the regulation of ET at the level of transcription. This information could be compared to the regulatory pathways of CT and other genes involved in lipid and cholesterol metabolism to establish the regulatory mechanisms for membrane biogenesis and lipid maintenance during normal development and in lipid-related pathological states.

SUMMARY OF THE INVENTION

It is an object of the present invention to provide a nucleotide sequence of a murine ET gene. It is yet another object of the present invention to provide a promoter sequence of the human ET gene.

The invention provides a gene encoding a protein having ethanolaminephosphate cytidylyltransferase activity consisting of a sequence selected from the group consisting of: (a) SEQ ID NO:1; (b) a degenerate sequence of SEQ ID NO:1 and (c) a sequence which hybridizes to the complement of SEQ ID NO:1 under stringent conditions.

Further, the invention provides a promoter of an ethanolaminephosphate cytidylyltransferase gene, said promoter consisting of a sequence selected from the group consisting of: (a) SEQ ID NO:2; (b) a sequence according to SEQ ID NO:2 having substitutions or deletions and maintaining promoter activity; and (c) a sequence which hybridizes to the complement of SEQ ID NO:2 under stringent conditions.

The gene and promoter according to the invention can be used to produce a transgenic mammal. The gene and promoter are useful in identifying, preventing, and treating diseases related to inappropriate phoshatidylethanolamine production.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

Embodiments of the present invention will now be described, by way of example only, with reference to the attached figures.

FIG. 2 is an alignment of amino acid sequences of rat ET (rET), human ET (hET), and the mouse ET (mET) proteins. The alignment illustrates the ET consensus motifs MIRNG and HYGH, conserved in the entire cytidylyltransferase superfamily.

FIG. 7 shows alignment of the positive clones for the 5'-end of human ET to the published human ET cDNA sequence. The sequence of the gene specific primer sequence, I2RP is underlined. The translational start codon of hET is in bold and underlined.

FIG. 8 shows the 5'-flanking (regulatory, promoter) region of the human ET (corresponding to SEQ ID NO: 2) with consensus cis-elements for the regulatory transcription factors.

DETAILED DESCRIPTION OF THE PREFERED EMBODIMENTS

Figure 1:
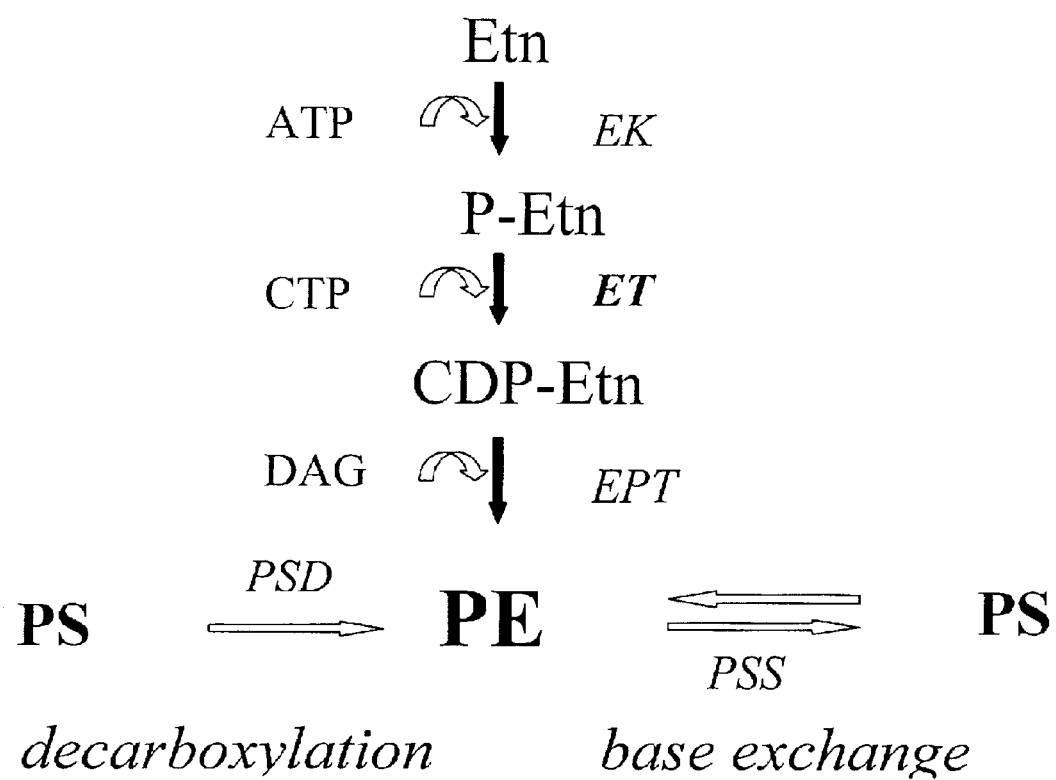
FIG. 1 shows a schematic representation of the three known biosynthetic pathways for phosphatidylethanolamine (PE) in mammalian cells.

This is the first characterization of the mouse and human CTP: phosphoethanolamine cytidylyltransferase genes. The isolated gene and promoter sequences are novel and do not match any other sequences in the mouse and human database. The mouse gene sequence is unique and distinct from the human gene sequence. The isolated gene and promoter have a number of applications within the biotechnology and pharmaceutical industries.

The invention is based on the screening of the mouse RP23 BAC (Bacterial Artificial Chromosome) library by using the 3'-end "overgo" cDNA sequence of the mouse ET.

Thirteen positive mouse ET clones were identified. The BAC clones were reamplified with different primers, and after subcloning into a PCR vector and sequencing all positive clones were identified, the mouse ET gene was reconstructed. The BAC clones encoding the full-length mouse ET gene were isolated. The murine ET gene and the 5' flanking (regulatory, promoter) region of the human ET gene were determined and are disclosed herein. The characterization of the overall structure for the murine and human ET genes as well as the localization of cis-DNA elements for transcription factors in the 5'flanking promoter region of the human gene are disclosed.

A gene according to the invention encoding a protein having ethanolaminephosphate cytidylyltransferase activity. The gene consists of a sequence selected from the group consisting of: (a) SEQ ID NO:1; (b) a degenerate sequence of SEQ ID NO:1 and (c) a sequence which hybridizes to the complement of SEQ ID NO:1 under stringent conditions. A portion of such a gene capable of encoding a protein having ethanolaminephosphate citidylyltransferase activity also falls within the scope of the invention. In the examples put forth herein, SEQ ID NO: 1 was isolated from mouse.

A promoter of an ethanolaminephosphate cytidylyltransferase gene according to the invention has a sequence selected from the group consisting of: (a) SEQ ID NO:2; (b) a degenerate sequence of SEQ ID NO:2 possessing promoter activity; and (c) a sequence which hybridizes to the complement of SEQ ID NO:2 under stringent conditions.

By a "degenerate sequence", it is meant a sequence in which a different codon is used to specify the insertion of the same amino acid in a peptide chain. Degenerate sequence codons can easily be determined by those of skill in the art. Further, sequences specifying codons which indicate a conservative substitution of an amino acid into a sequence, which conservative substitution does not effect the resulting protein function also fall within the scope of the invention. The effect of such conservative substitutions can be determined according to functional tests.

By "stringent conditions", it is meant hybridization conditions of temperature and concentration which ideally result in duplex DNA molecules formed only between strands in which the vast majority of nucleotide bases are paired.

An advantage of knowing the sequence of the isolated mouse ET gene according to the invention is that the genetic control of PE formation can be determined for effects on PE availability for membranes during cell growth, determination of the role of PE in performance of specialized functions such as blood clotting and in response to disease states such as cancer. PE formation requires the action of the ET gene product. The possession of the genomic sequence and the knowledge of the primary structure of this gene allows manipulation of the structure and function of this gene. By manipulation of the gene, it is possible to make transgenic animals by either mutating the gene, increasing gene expression, or deleting all or a portion on the gene to produce a knock-out mouse strain. Further, a transgenic animal so formed could be cross-bred with other transgenic animals which also provide models of disease.

By making transgenic animals or 'knocking-out' this gene, it will be possible to defined the molecular interactions regulating the production of this enzyme at the genetic level and its relationships with other lipid genes. This has applications for diagnosis, prevention and therapy of diseases related to inappropriate PE production, such as Zellweger's syndrome, or lipid-related diseases such as cardiovascular disease and obesity.

Transgenic animals containing the ET promoter fused to a reporter gene (e.g., green-fluorescent protein, luciferase) can be produced according to the invention. Such transgenic animals may include regulatory sequences or other mechanisms to allow for basal and tissue-specific transcription of this gene. This will allow analysis of the signalling pathways required for gene expression during normal cell growth and malignant transformations.

As used herein, the following abbreviations are defined as follows. BAC, bacterial artificial chromosome; CDP-etn: CDP-ethanolamine; DAG: diacylglycerol; DEPC, diethyl pyrocarbonate; EK: ethanolamine kinase; EPT: ethanolaminephosphotransferase; Etn: ethanolamine; PCR, polymerase chain reaction; PtdCho, phosphatidylcholine; PtdEtn, phosphatidylethanolamine; PtdSer, phosphatidylserine; ET, CTP:ethanolaminephosphate cytidylyltransferase; RT-PCR, reverse transcriptase-mediated PCR; RACE, rapid amplification of cDNA ends; PC, phosphatydylcholine; P-etn: phosphoethanolamine; CT, CTP: cholinephosphate cytidylyltransferase; PE, phosphatydylethanolamine; PS, phosphatydylserine; PSD: PS decarboxylase; PSS: PS synthase; DAG, diacylglycerol; PEtn, phosphoethanolamine; Etn, ethanolamine; CDP-Etn, cytidinediphosphate ethanolamine; EK, ethanolamine kinase; EPT, CDP-ethanolamine: 1,2-diacylglycerol ethanolamine phosphotransferase; PSS, phosphatylylserine synthase; APC, activated protein C; ER, endoplasmic reticulum; 5'-UTR, 5'-untranslated region; and PCR, polymerase chain reaction.

EXAMPLES

The following material and methods were applied in illustrating the examples described below.

Materials. Restriction endonucleases, Taq DNA polymerase, dNTPs, PCR reagents, the Concert™ plasmid miniprep kit, Triazol™, 18-oligo-dT primers, Superscript™ II reverse transcriptase, and other molecular biology reagents were obtained from Life Technologies Inc. (Burlington, ON, Canada). Wizard™ miniprep kit or Wizard™ maxiprep kit were from Promega (Madison, Wis.) and the 5'RACE kit (version 2.0) from Gibco BRL. The cloning of PCR products was performed either by the TA cloning kit (Invitrogen, Mississauga, ON, Canada) or QIAGEN PCR cloning kit and the QIAprep™ Spin Miniprep Kit was used for purification (Qiagen). All other reagents were obtained from Sigma (Oakville, ON, Canada) or Fisher Scientific (Nepean, ON, Canada).

Mouse Library Screening. The mouse RPCI23 genomic library from C57BL/J6 female (Roswell Park Cancer Institute, Buffalo) was screened. An individual probe screening of seven filter sets was performed with an overgo-generated probe specifically designed from a mouse EST (GenBank™: BC003473) and compared to human ET gene and marker (stSG12878) sequence of Chromosome 17 (GenBank: AC069004, BAC clone: RP11-498C9). An overgo that corresponded to the 3'-untranslated region of BC003473 at position 1342–1381 bp (5'-TGTCAGCTCACACAATTCCAAAGGAAACTGGCCTT-GCTG-3'; SEQ ID NO: 3) was used to design two complementary primers, BC003473-OVa: TGTCAGCTCACA-CAATTCCAAAGG (SEQ ID NO: 4) and BC003473-Ovb: TCAGCAAGGCCAGTTTCCTTTGGA (SEQ ID NO: 5), that act as primers for each other in a labelling reaction. After the second screen, 5 out of 12 BAC clones (Cloning vector pBACe3.6) were obtained corresponding to the sequence of the murine ET gene. The BAC45A04 clone from the RPCI23 genomic library was used for further analysis.

BAC and plasmid DNA preparation and analysis. BAC DNA was isolated using either a Qiagen midi-prep kit (tip 100) or by standard methodology according to Sambrook and Russell (Molecular Cloning, a laboratory manual, 3rd Ed.). Plasmid DNA was isolated with a Wizard™ miniprep kit, Wizard™ maxiprep kit and/or by the Concert™ miniprep kit. Screening and characterization of the genomic BAC (bacterial artificial chromosome) clones for the murine ET gene were performed by PCR and sequencing. PCR reactions were performed under the following conditions: the initial denaturation for 3 min at 94° C., plus 30 cycles of denaturation at 94° C. for 30 sec, annealing at 58° C. for 30 sec, and extension at 72° C. for 1 min, including a final extension at 72° C. for 8 min. The PCR products were cloned into a PCR vector from the Qiagen PCR cloning kit and subsequently sequenced in both directions by using the vector specific primers and/or the ET specific primers.

Primer Design and Sequencing. All primers for the mouse and human ET, except the abridged anchor primer AAP were synthesized by the Laboratory Services Division at the University of Guelph Molecular Supercenter. AAP was supplied in the 5'RACE kit. DNA sequencing was performed at the University of Guelph Molecular Supercenter.

RNA isolation and RT-PCR analysis. Murine tissues (adipose, brain, kidney, liver, lung, spleen and testis) from p57/BL mice were snap-frozen in nitrogen and total RNA was isolated using Triazol™ reagent according to manufacturers instructions. RNA was evaluated by performing electrophoresis on 1% formaldehyde gels with ethidium bromide. Total RNA was reverse-transcribed using an 18-oligo-dT primer and Superscript™ II reverse transcriptase, as per manufacturers instructions. Briefly, 5 µg of total RNA was incubated at 70° C. for 10 min in the presence of 1 µl of primer (10 µM). After a brief centrifugation, 4 µl of "first strand buffer", 2 dithiothreitol (0.1 M) and 1 µl of dNTP mix (10 mM) were added and 42° C. for 2 min prior to addition of Superscrip™ reverse transcriptase (1 µl) another incubation at 42° C. for 45 min. The reaction was terminated by incubation at 70° C. for 15 min. PCR was performed on the cDNA products by using primers specific for ET. The identity of the products was confirmed by sequencing.

Identification of the human ET transcriptional start site. The transcriptional start site of human ET gene was determined by the 5'RACE methodology. Total RNA from human hepatoma cells HepG2 (Geneka Biotechnology) was subjected to a reverse transcription using oligo(dT) primer and Superscript™ II reverse transcriptase (RT), following the manufacturers' instructions. The newly synthesized cDNA was purified and tailed with a poly(dC) using reverse terminal deoxynucleotidyl transferase (rTdT). The 5'-end tailed fragment of the human ET was then amplified by PCR: 20 mM Tris-HCl, 50 mM KCl, 1.5 mM MgCl2, 200 µM dNTPs, 400 µM abridged anchor primer (annealing to the poly(dC) tail), 400 µM RP2AC gene specific reverse primer (Table 1), 8% glycerol (to increase primer binding specificity), 2.5 units Taq polymerase, and 10 µl tailed cDNA template, with a final volume of 50 µl. This reaction was subjected to a 3 min initial denaturation at 94° C., followed by 35 rounds of amplification each consisting of a 45 s denaturation at 94° C., a 30 s primer annealing step at 50° C., and a 90 s primer extension at 72° C. The reaction was terminated after a 10 min final extension at 72° C. Nested PCR was performed using 3 µl of the above PCR mixture, amplified using the AAP primer and either I2RP or RP1AC gene specific reverse primer (Table 1) under the same conditions. Table 1 provides a list of human ET specific primers used in the 5'-RACE analysis.

TABLE 1

Human ET Specific Primers

| Primer Name | Sequence (5' to 3') | Position (on D84307) | SEQ ID NO |
|---|---|---|---|
| RP2AC | TCTCCTGGCTGCTGTGATG | +544 to +562 | 6 |
| RP1AC | CCGTGAACACAGAAGTCACAGT | +383 to +404 | 7 |
| I2RP | CACCTCGTCCACCCATTT | +316 to +333 | 8 |
| AAP | GGCCACGCGTCGACTAGT ACGGGIIGGGIIGGGIIG | Poly(dC) tail | 9 10 |
| PCR2.1FP | CAGGAAACAGCTATGAC | ~75 bp upstream of PCR insert | 11 |
| PCR2.1RP | TAATACGACTCACTATAGGG | ~75 bp downstream of PCR insert | 12 |

Cloning of the Mouse ET Genomic Products and Human ET 5'-End Products: Subcloning of the BAC45A04 mouse genomic sequence was performed into a PCR cloning vector from Quiagen. Clones were tested for the presence of ET sequence and sequencing was performed on 6 overlapping mouse genomic regions using different set of overlapping primers as shown in Table 2 and FIG. 3. Human ET 5'-end products of 5'RACE were cloned into the pCR2.1 cloning vector (TA Cloning Kit, Invitrogen). Screening of the inserts was determined by PCR of the miniprep DNA in order to determine sizes of the fragments inserted into the pCR2.1 vector. 3 µl of miniprep DNA template was amplified using the PCR protocol employed for 5'RACE except glycerol was not used in the reaction and the primer annealing step was conducted at 55° C. The authenticity of fragments of desired lengths were confirmed by sequencing, the result of which is illustrated in FIG. 7.

TABLE 2

Location and individual size of the protein coding sequence (exons) in the genomic clone BAC 45A04 that correspond to the murine ET coding sequence.

| Exon No. | Position in cDNA[a] | Exon Size | Location in SEQ ID NO:1[d] |
|---|---|---|---|
| 1 | 45[b]–133 | 5'UTR + 88 | 1–89 |
| 2 | 134–222 | 88 | 1918–2006 |
| 3 | 223–384 | 189 | 2402–2565 |
| 4 | 385–451 | 70 | 3456–3525 |
| 5 | 452–536 | 84 | 4131–4217 |
| 6 | 537–581 | 44 | 4433–4479 |
| 7 | 582–635 | 53 | 4774–4828 |
| 8 | 636–774 | 138 | 5255–5394 |
| 9 | 775–857 | 82 | 5773–5856 |
| 10 | 858–935 | 77 | 6151–6229 |
| 11 | 936–1001 | 65 | 6443–6510 |
| 12 | 1002–1067 | 65 | 6678–6745 |
| 13 | 1068–1156 | 88 | 6892–6982 |
| 14 | 1154–1259[c] | 105 + 3'UTR | 7086–7188 |

[a]Position and sequence of exons are based on a BLAST alignments of the BAC45A04 mouse genomic clone with the putative ET cDNA clone BC003473;
[b]the cDNA sequence # 43 correspond to +1(A) of the ATG translation start codon; 5- and 3'- UTRs are 5'- and 3'- untranslated regions and they are not included in the SEQ ID No:1;
[c]the cDNA sequence # 1259 is G from the TAG translation stop codon;
[d]BAC45A04

Analysis of the ET Gene Regulatory Region. The 5' sequence proximal to the transcriptional initiation site was obtained by using human ET specific primers for amplifying human genomic DNA isolated from MCF-7 human mammary carcinoma cell line and/or a BAC clone RP11498C9 (GenBank™ AC069004) obtained from The Sanger Sequencing Center, UK. The sequence of the ET promoter region (SEQ ID NO:2) was evaluated using the Transfac™ transcription factor database located at http://pdap1.trc.rwcp.or.jp/research/db/TFSEARCH.html.

Example 1

Cloning and Exon-Intron Organization of the Murine ET Gene

Figure 3:
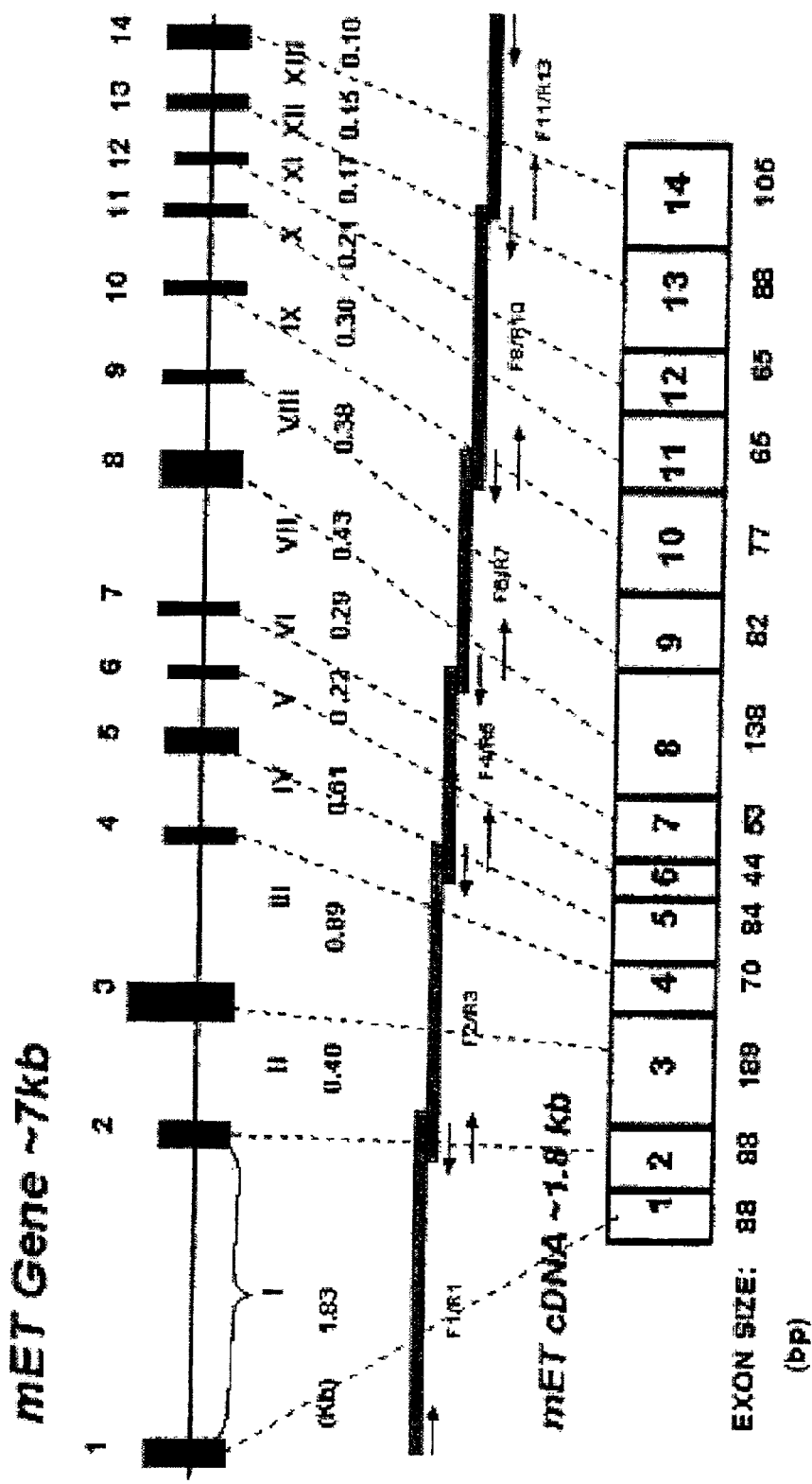
FIG. 3 is the structure and organization of the murine ET gene.

FIG. 3 shows the structure and organization of the murine ET gene. Schematic representation of both murine ET gene and cDNA are shown. Solid horizontal lines and solid boxes represent Introns and Exons, respectively. Numbers and sizes of exons (1–14) and introns (I–XIV) are also shown. The position and size of exons within the murine ET cDNA are indicated in the lower part of the FIG. 3. The translational start site codon, ATG, encoding the protein is at the beginning of Exon 1 and the stop codon, TGA, is in Exon 14 at position 1257–1259. The mid section displays the cloning strategy, the positions of primers and six overlapping clones used for the genomic sequence analysis.

Several putative ET clones were isolated from the mouse BAC genomic library RPCI23 by using the "overgo" screening methodology. After performing a second screening with the 5'- and 3'-end specific primers shown in Table 3, one clone from the library, namely BAC45A04, that contained both 5'- and 3'-ends was identified, suggesting the presence of the entire ET gene in this clone. Further analysis of this clone was conducted by PCR amplification, subcloning, and sequencing by using gene-specific primers shown in Table 3 from six overlapping regions, as shown in FIG. 3. The complete exon/intron structure of the mouse ET gene was successfully identified, as shown in FIG. 3, Table 2 and Table 4, and the sequence the is shown as SEQ ID NO: 1.

TABLE 3

Sequences and positions of PCR primers used for identification and amplification of the murine ET gene[a]

| Primer | 5'-Sequence-3' | Position in cDNA | Exon # | SEQ ID NO |
|---|---|---|---|---|
| Forward: | | | | |
| F1 | GGATTTGCGGGGGGCCTCCG | 20–39 | 1 | 13 |
| F2 | ACGGCAGGCACGGGCCATGGG | 170–190 | 2 | 14 |
| F4 | ACGCTGACAGTAGACGGCCG | 393–412 | 4 | 15 |
| F6 | GGAGATGTCCTCTGAGTACCG | 536–556 | 6 | 16 |
| F8 | TTCTGGGAAGGAGCCCCAGCC | 710–730 | 8 | 17 |
| F11 | ACCATACTCCGTGACAGCGG | 962–981 | 11 | 18 |
| Reverse: | | | | |
| R1 | GTATGCACACCCACGATGAGG | 217–197 | 2 | 19 |
| R3 | CTCCCAGCCTGCTTCACTTCC | 445–425 | 4 | 20 |
| R5 | TTCCAAAACTGTCAGCATATTCC | 579–557 | 6 | 21 |

TABLE 3-continued

Sequences and positions of PCR primers used for identification and amplification of the murine ET gene[a]

| Primer | 5'-Sequence-3' | Position in cDNA | Exon # | SEQ ID NO |
|---|---|---|---|---|
| R7 | GGCACCAGCCACATAGATGAC | 761–741 | 8 | 22 |
| R10 | ACCTTGAAGTGATTCAGGAGC | 1003–983 | 11 | 23 |
| R13 | GGTGGGCACAGGGCAAGGGC | 1304–1285 | 14 | 24 |

[a]According to the putative murine ET cDNA sequence, GenBank ™ BC003473

The sequenced ET gene is 7,188 kb in length starting from the ATG translation start codon and ending at the TGA translation stop codon. The gene is composed of 14 exons interrupted by 13 introns shown in FIG. 3 and Tables 2 and 4. The sizes of exons range from 44 (Exon 6) to 189 bp (Exon 3) and Exon 14 contains the TGA stop codon.

TABLE 4

The location and size of the non-coding, intervening sequence (introns) in the genomic clone BAC45A04 and the exon-intron boundaries within the murine ET gene.

| 5'-Splice Donor[a] | Intron No. and Intron Size (bp) | 3'-Splice Acceptor | Intron Positions SEQ ID NO: 1 |
|---|---|---|---|
| GGCTG/*GTGAG* | 1 (1829) | *CACAG*/CTATG | 90–1917 |
| GGATG/*GTAAG* | 2 (395) | *CCTAG*/AGGAG | 2007–2402 |
| CGGCA/*GTGAG* | 3 (891) | *TCTAG*/ATGAC | 2565–3456 |
| TACAG/*GTAGG* | 4 (608) | *CCCAG*/AGAGT | 3523–4131 |
| GCCAG/*GTGAG* | 5 (216) | *TGCAG*/GAGAT | 4217–4433 |
| GAAAG/*GTGAG* | 6 (294) | *TGTAG*/CCCCC | 4479–4773 |
| CCCAG/*GTGAC* | 7 (427) | *AACAG*/TGCCC | 4828–5255 |
| GTTCC/*GTATC* | 8 (379) | *TATAG*/ACATC | 5394–577 |
| ACCAG/*GTCTC* | 9 (295) | *CCTAG*/GAAGT | 5856–6151 |
| GCCGG/*GTAAG* | 10 (214) | *CGCAG*/TATGT | 6229–6443 |
| TCAAG/*GTGAG* | 11 (168) | *TCCAG*/GTGGA | 6510–6678 |
| ACCAG/*GTGGG* | 12 (147) | *TCCAG*/GAGCC | 6745–6893 |
| AACAG/*GTGTG* | 13 (103) | *CCCAG*/GCTGG | 6982–7085 |

[a]The intron sequences are shown in italic and underlined.

Sequencing of six overlapping regions showed that the introns in the mouse gene were bellow 2 Kb, which allowed an accurate description of all introns present by using PCR amplification and sequencing. The introns range in size from 103 bp (the last intron, Intron XIII) to 1829 bp (the first intron, Intron I) as shown in FIG. 3 and Table 4. The organization of the mouse gene is different from that of the human ET gene as shown in Table 5. Information for the human Chromosome 17, Locus Link for human ET gene, changes frequently, and can be found at http://www.ncbi.nlm.nih.gov/LocusLink/LocRpt.cgi?1=5833. The human gene contains 15 exons and 14 introns: the sizes of exons are between 36 bp (Exon 13) and 958 bp (Exon 14) and the sizes of introns are between 128 (Intron 12) and 7944 (Intron 14) as shown in Table 5.

TABLE 5

Intron sizes of human ET and the exon-intron boundaries within this gene obtained from the GeneBank sequence contingent at Chromosome 17 NT_01045.

| 5'-Splice Donor* | Intron No. | Intron Size (bp) | 3'-Splice Acceptor |
|---|---|---|---|
| GGCTG/*GTGAG* | 1 | (835) | *CACAG*/CTATG |
| CGATG/*GTAAG* | 2 | (476) | *CCTAG*/AGGAG |
| CGGCA/*GTGAG* | 3 | (240) | *CTTAG*/ATGAC |
| TACAG/*GTGAG* | 4 | (709) | *CCTAG*/AGAAT |
| GCCAG/*GTGAG* | 5 | (174) | *TGCAG*/GAGAT |
| GCAAG/*GTGAG* | 6 | (655) | *TGCAG*/TGCCC |
| GTTCC/*GTATC* | 7 | (213) | *TGCAG*/ACATC |
| ACCAG/*GTCAC* | 8 | (285) | *CGCAG*/GAGGT |
| GCCGG/*GTGAG* | 9 | (364) | *CACAG*/TACGT |
| TCAAG/*GTGAG* | 10 | (222) | *TCCAG*/GTGGA |
| ACCAG/*GTGGG* | 11 | (244) | *TGTAT*/GAGGC |
| AGCTC/*GTCTT* | 12 | (128) | *GGGAA*/GGCGG |
| AAGGC/*AGGTG* | 13 | (7944) | *CCCCT*/GCCTT |

The invention also establishes the exon-intron boundaries of the mouse and human genes as shown in Table 4 and Table 5, respectively. The boundary sequences at the 5'- and 3'-ends of all the mouse introns are GT and AG, respectively. These are consensus sequences for pre-mRNA splicing donor and acceptor sites (52)

Example 2

Identification of Transcriptional Initiation Site for the Human ET Gene

Figure 4:
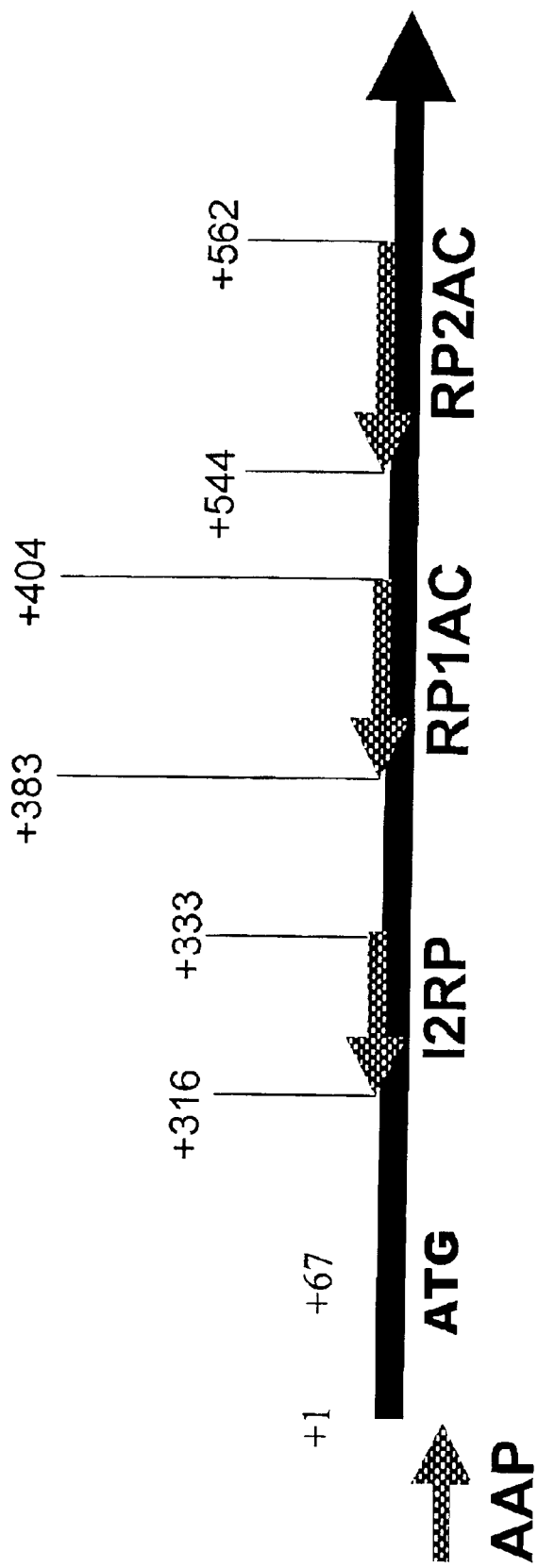
FIG. 4 illustrates the determination of transcription initiation site of human ET gene. The 5'RACE strategy showing the location of human ET-specific primer binding sites is provided.
Figure 5:
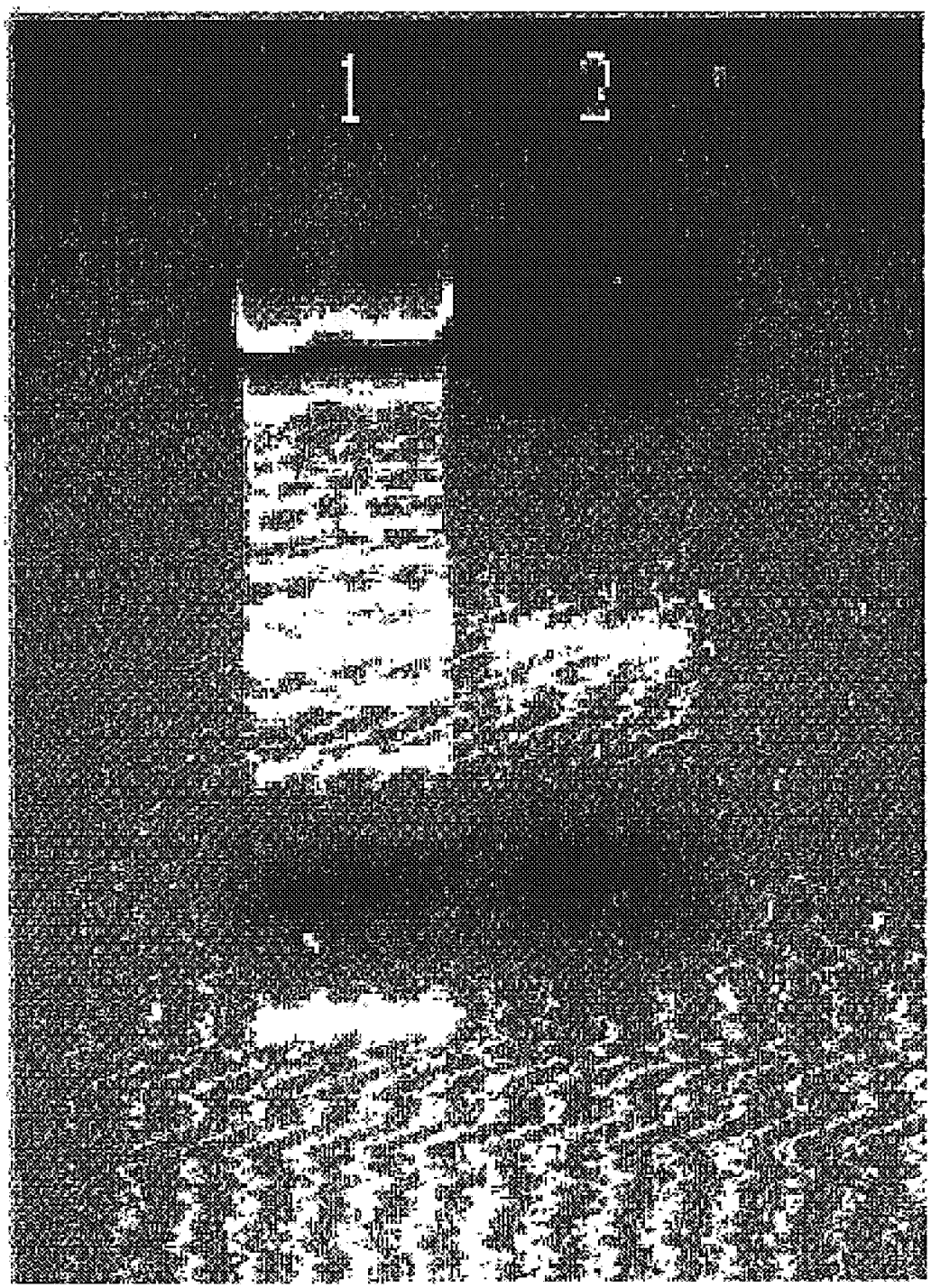
FIG. 5 shows results of the PCR reaction for the 5'RACE of human ET cDNA using the abridged anchor primer, AAP, and the gene specific reverse primer RP2AC.
Figure 6:
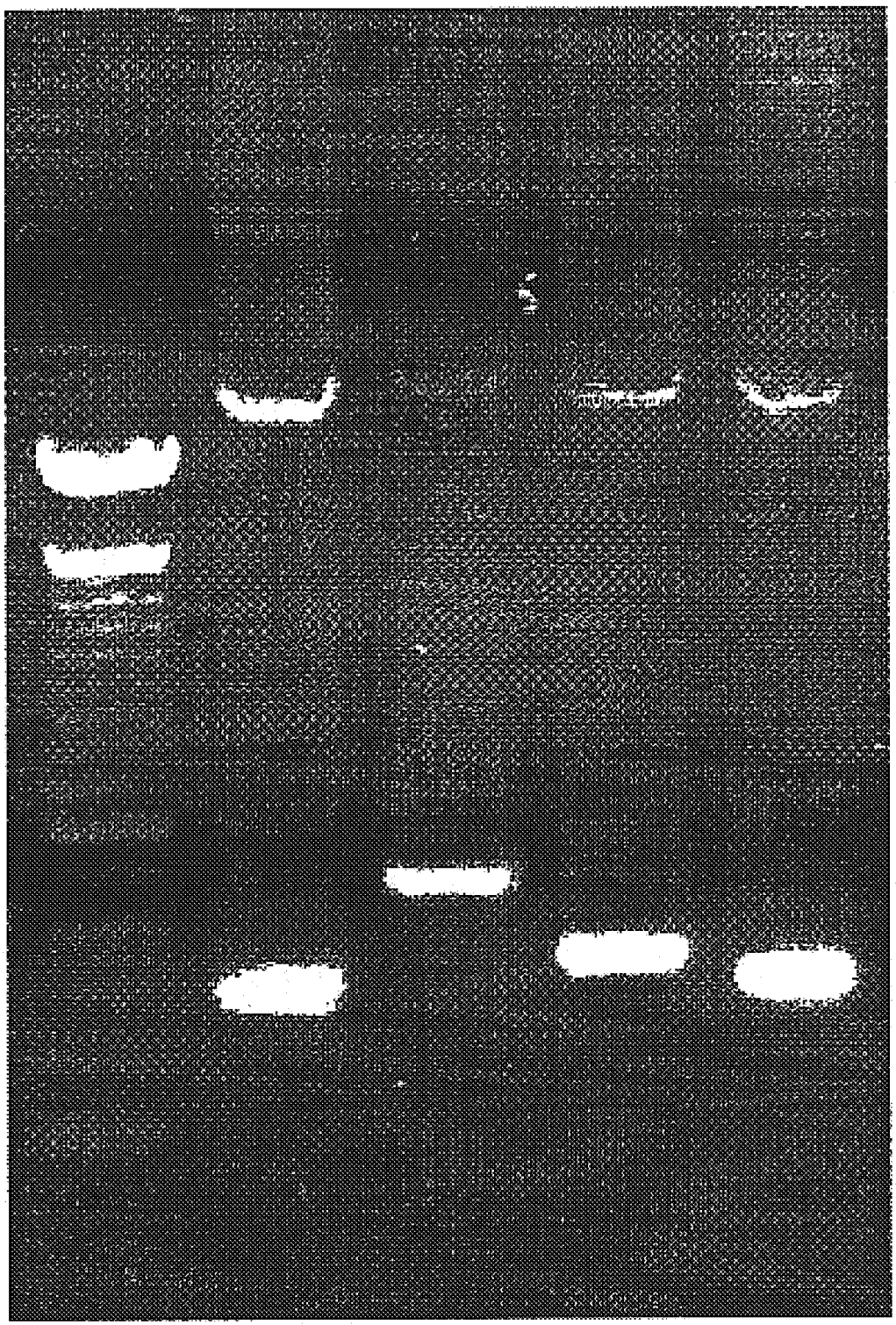
FIG. 6 shows identification of positive clones for the 5'-end of human ET.

FIG. 4 to FIG. 6 illustrate steps involved in the determination of transcription initiation site of human ET gene.

FIG. 4 shows 5'RACE strategy illustrating the location of human ET-specific primer binding sites. The abridged anchor primer, AAP, binds to the dCTP tail of the cDNA. Gene specific reverse primers of human ET, I2RP, RP1AC, and RP2AC, bind to the cDNA at positions +316/+333, +383/+404, and +544/+562, respectively. These positions correspond to the published sequence for the human ET cDNA (GenBank™ D84307).

FIG. 5 shows the results of the PCR reaction for the 5'RACE of human ET cDNA using the abridged anchor primer, AAP, and the gene specific reverse primer RP2AC. The 5'-RACE analysis, using the AAP and RP2AC primers, produced one prominent band at ~600 bp as shown in lane 2 of FIG. 5, which coincides with the binding site for the RP2AC primer on the published human ET cDNA sequence (GenBank™ D84307). In FIG. 5, lane 1 represents a 100 bp ladder and the bright band corresponds to a 600 bp fragment.

To confirm that the 5'-end for human ET is being amplified, two nested PCR reactions were utilized using one reaction with the RP1AC reverse primer, and the second reaction using the I2RP reverse primer. FIG. 6 shows the results of one PCR screening of colonies containing the inserts from the nested PCR reaction. Only lane 3 holds the PCR product size of a length, of about 500 bp, that corresponds to the length of the 5'end of human ET including the 5' and 3' flanking regions that would be amplified from the pCR2.1 vector using pCR2.1 specific primers binding to 5' and 3' flanking regions of the insert area. Further screening yielded three colonies that contained inserts of a desired length. They were all further confirmed for the 5'-end of human ET by sequencing.

FIG. 7 represents the sequence alignment of three positive clones with the published sequence for the human ET cDNA (GenBank™ D84307). The clones, named hET-C5.3, C2.3, and C1.1, contained the sequence for human ET from positions +23/+333, +111/+333, and +109/+333, respectively. Position +333 corresponds to the last nucleotide of the nested I2RP reverse primer. Clone hET C5.3, having a 5'-end beginning at position +23 in comparison to the published human ET cDNA, represents one transcriptional start site of human ET. The ATG translational start codon for the gene lies downstream of the start site, at position +67. Clones hET C2.3 and C1.1, whose 5'-ends begin at positions +109 and +111, respectively, may represent a second transcription start site. There is an ATG codon at position +149 but it seems unlikely that it is in fact a true start site for human ET gene. A translational start at this position would not include the MIRNG motif conserved in all ET proteins, shown in FIG. 2. This suggests that the clone hET-C5.3 is representative of the 5'end of the human ET cDNA and is also representative of the true transcriptional start site of the human ET gene. This evidence also suggests that the promoter of the human ET gene lies just upstream, in the 5' flanking sequence of the beginning of exon 1.

Example 3

The 5' Flanking Region of the Human ET Gene and the Overall Gene Structure

The structure for the human ET gene has been characterized using data obtained from the human genome project (BAC clone RP11498C9, GenBank™ AC069004, and human ET cDNA, GenBank™ NT_010845, sequence alignments). Human ET gene consists of 14 exons (total size ~20 Kb) the first 13 exons of which are separated by relatively small introns (~500 bp) as shown in Table 5. Intron 13 is comparatively larger than the rest (~12 kb, Table 4), separating exon 14 from the rest of the gene. From the results of 5'RACE according to the invention, the ATG start codon lies 45 bp downstream of the transcription start site. The promoter region of human ET, which lies immediately upstream of exon 1, is approximately 500 bp and has the sequence shown in SEQ ID NO: 2 and FIG. 8. Upstream of this region lies the coding sequence of another gene.

FIG. 8 shows 5'-flanking (regulatory, promoter) region of the human ET (SEQ ID NO: 2) with consensus cis-elements for the regulatory transcription factors. In italics is the exon I of human ET with an arrow pointing to the transcription start site determined by 5'RACE. In bold and underlined is the ATG translation start codon. Underlined in certain boxes are the consensus binding sites for transcription factors Sp1, MyoD, Ap1, Ap4, AP2, NFkB, CAAT binding protein CBP, and NF1.

Using TRANSFEC™ transcription factor database, the transcription factor binding sites for the promoter region of the human ET were determined. This analysis led to the identification of multiple binding sites for several families of transcription factors, including the Sp family, the AP family, and the MyoD family. Eleven binding sites for the Sp-1 transcription factor were discovered according to the invention, which lie immediately upstream of the transcription start site in a very GC rich area in the sequence. The Sp-1 family of transcription factors, which binds GC boxes, can both initiate and regulate transcription, and offers both ubiquitous and regulated expression of human ET (53). The Sp family of transcription factors play an important role in the expression of the CT gene (54). A CAAT box is located approximately 100 bp from the transcriptional start site. Other transcription factor binding sites that have been identified may be utilized in tissue-specific expression of ET gene. The presence of several cis-elements for binding transacting factors and occurrence of a coding region for another gene upstream of SEQ ID NO: 2 indicates that the isolated DNA of SEQ ID NO: 2 is a promoter.

The isolation of the promoter region of human ET is important for the understanding of the regulation of human ET expression. The identification of this region promotes understanding of the coordination of expression of other lipogenic genes, whose regulation must be strictly regulated to ensure that phospholipid turnover is maintained.

The above-described embodiments of the present invention are intended to be examples only. Alterations, modifications and variations may be effected to the particular embodiments by those of skill in the art without departing from the scope of the invention, which is defined solely by the claims appended hereto.

REFERENCES

1. Bazzi, M. D., Youakim, M. A., and Nelsestuen, G. L. (1991) Biochemistry 31, 1125–1134.
2. Bogdanov, M., Umeda, M., and Dowhan, W. (1999) J. Biol. Chem. 274, 12339–12345.
3. Engelmann, B., Schaipp, B., Dobner, P., Stoechelhubert, M., Kogl, C., Siess, W., and Hermetter, A. (1998) J. Biol. Chem. 273, 27800–27808.
4. Gilbert, G. E., and Arena, A. A. (2000) J. Biol. Chem. 270, 18500–18505.
5. Smirnov, M. D., Triplett, D. T., Comp, P. C., Esmon, N. L., and Esmon, C. T. (1995) J. Clin. Invest. 95, 309–316.
6. Mileykovskaya, E., Sun, Q., Margolin, W., and Dowhan, W. (1998) J. Bacteriol. 180, 4252–4257.
7. Emoto, K., Kobayashi, T., Yamaji, A., Aizawa, H., Yahara, I., Inoue, K., and Umeda, M. (1996) Proc. Natl. Acad. Sci. 93, 12867–12872.
8. Emoto, K., Toyama-Sorimachi, N., Karasuyama, H., Inoue, K., and Umeda, M. (1997) Exp. Cell Res. 232, 430–434.
9. Ellens, H., Siegel, D. P., Alford, D., Yeagle, P. L., Boni, L., Lis, L. J., Quinn, P. J., and Bentz, J. (1989) Biochem. 28, 3692–3703.
10. Aoki, Y., Uenaka, T., Aoki, J., Umeda, M., and Inoue, K. (1994) J. Biochem. 116, 291–297.
11. Menon K. A., and Stevens, I. V. (1992) J. Biol. Chem., 267, 15277–15280.
12. Menon, K. A., Eppinger, M., Mayor, S., and Schwarz, T. R. (1993) EMBO J., 12, 1907–1914.
13. Kamitani, T., Menon, K. A., Hallaq, Y., Waren, D, C., and Yeh, T. E. (1992) J. Biol. Chem., 267, 24611–24619.
14. Hong, Y., Maeda, Y., Watanabe, R., Ohishi, K., Mishkind, M., Riezman, H., and Kinoshita, T. (1999) J. Biol. Chem., 274, 35099–35106.
15. Van den Bosch, H., Schutgens, R. B. H., Wanders, R. J. A., and Tager, J. M. (1992) Annu. Rev. Biochem. 61, 157–197.
16. Jira, W., and Spiteller, G. (1996) Chem. Phys. Lipids. 79, 95–100.
17. Fallbrook, A., Tur, 1–8.enne, S. D., Mamalias, N., Kish, S. J., and Ross, B. M. (1999) Brain Res. 834, 207–210.
18. Xu, L., Byers, M. D., Palmer, C. St. B. F., Spence, W. M., and Cook, W. H. (1991) J. Biol. Chem., 266, 2143–2150.
19. Snyder, F. (1985) In Biochemistry of Lipid and Membranes (Vance, D. E. and Vance, J. E. Eds.) pp 271–298, Benjamin Commings Publishing Co., Menlo Park, Calif.
20. Porter, T. J., and Kent, C. (1990) J. Biol. Chem. 265, 414–422.
21. Lee, T. C. (1998) Biochim. Biophys. Acta, 1394, 129–145.
22. Datta, S. N., Golder, N. G, Wilson, N., and Hajra, K. A. (1984) New Engl. J. Med., 311, 1080–1083.
23. Schrakamp, G., Schutgens, H. B. R., Wanders, A. J. R. Heymans, A. S. H., Tager, M. J. and Van den Bosch, H. (1985) Biochim. Biophys. Acta, 833, 170–174.
24. Ravandi, A., Kuksis, A., and Shaikh, A. N. (1999) J. Biol. Chem., 274,16494–16500.
25. Ishidate, K., Iida, K., Tadokoro, K., and Nakazawa, Y. (1985) Biochim. Biophys. Acta. 833, 1–8.
26. Tadokoro, K., Ishidate, K., and Nakazawa, Y. (1985) Biochim. Biophys. Acta. 835, 501–513.
27. Uchida, T., and Yamashita, S. (1992) J. Bio. Chem. 267, 10156–10162.
28. Aoyama, C., Nakashima, M., Matsui, M., and Ishidate, K. (1992) Biochim. Biophys. Acta. 1390, 1–7.
29. Aoyama, C., Yamazaki, N., Terada, H., and Ishidate, K. (2000) J. Lipid Res. 41, 452–464.
30. Verneulen, P. S., Geelen, M. J. H., Tijburg, L. B. M., and van Golde, L. M. G. (1997) Advances in Lipobiology. 2, 287–322.
31. Polokoff, M. A., Wing, D.C., and Raetz, C. R. H. (1981) J. Biol. Chem. 256, 7687–7690.
32. Vance, J. E., and Vance, D. E. (1992) J. Biol. Chem. 263, 5898–5909.
33. Hjelmstad, R. H., and Bell, R. M. (1991) J. Biol. Chem. 266, 5096–5103.
34. Henneberry, A. L., and McMaster, C. R. (1999) Biochem. J. 339, 291–298.
35. Tijburg, L. B. M., Houweling, M., Geelen, M. J. H., and van Golde, L. M. G. (1987) Biochim. Biophys. Acta. 922, 184–190.
36. Vermeulen, P. S., Geelen, M. J. H., and van Golde, L. M. G. (1994) Biochim. Biophys. Acta. 1211, 343–349.
37. Van Hellemond, J. J., Slot, J. W., Geelen, M. J., van Golde, L. M., and Vermeulen, P. S. (1994) J. Biol. Chem. 269, 15415–15418.
38. Vermeulen, P. S., Tijburg, L. B. M., Geelen, M. J. H., and van Golde, L. M. G. (1993) J. Biol. Chem. 268, 7458–7464.
39. Min-Seok, R., Kawamata, Y., Nakamura, H., Ohta, A., and Takagi, M. (1996) J. Biochem. 120, 1040–1047.
40. Nakashima, A., Hosaka, K., and Nikawa, J. (1997) J. Biol. Chem. 272, 9567–9572.
41. Bladergroen, B. A., Houweling, M., Geelen, M. J. H., and van Golde, L. M. G. (1999) Biochem. J. 343, 107–114.
42. Bork, P., Holm, L., Koonin, E. V., and Sander, C. (1995) Proteins 22, 259–266.
43. Bladergoen, B. A., Houweling, M., Geelen, M. J. H., and Van Golde, L. M. G. (1999) Biochem. J., 343, 107–114.
44. Sugumoto, H., Bakovic, M., Yamashita, S., and Vance, D. E. (2001) J. Biol. Chem. 276, 12338–12344.

45. Mallampalli, R. K., Ryan, A. J., Salome, R. G., and Jackowski, S. (2000) J. Biol. Chem. 275, 9699–9708.
46. Lykidis, A., Baburina, I., and Jackowski, S. (1999) J. Biol. Chem. 274, 26992–27001.
47. Lykidis, A., Murti, K. G., and Jackowski, S. (1998) J. Biol. Chem. 273, 14022–14029.
48. Bladergroen, B. A., and van Golde, L. M. G. (1997)) Biochim. Biophys. Acta. 1348, 91–99.
49. Kikuchi, K., Sakai, K., Suzuchi, T., and Takama, Z. (1999) Comp. Biochem. Physiol. 124B, 1–6.
50. Xu, L., Byers, M. D., Palmer, C. St. B. F., Spence, W. M., and Cook, W. H. (1991) J. Biol. Chem. 266, 2143–2150.
51. Lee, T. (1998) Biochim. Biophys. Acta. 1398, 129–145.
52. Mount, S. M. (1982) Nucleic Acid Res., 10, 459–472.
53. Lania, L., Majello, B., and DeLuca, P. (1997) Int. J. Biochem. Cell Biol. 29, 1313–1323.
54. Bakovic, M., Waite, K. A., and Vance, D. E. (2000) J. Lipid Res. 41, 583–594.

What is claimed is:

1. An isolated gene encoding a protein having ethanolaminephosphate cytidylyltransferase activity consisting of a sequence selected from the group consisting of:

(a) SEQ ID NO:1; and (b) a degenerate sequence of SEQ ID NO:1.

2. The isolated gene according to claim 1 consisting of SEQ ID NO:1.

3. An isolated promoter of an ethanolaminephosphate cytidylyltransferase gene, said promoter consisting of a sequence according to SEQ ID NO:2.

* * * * *

SEQUENCE LISTING

<160> NUMBER OF SEQ ID NOS: 24

<210> SEQ ID NO 1
<211> LENGTH: 7188
<212> TYPE: DNA
<213> ORGANISM: Mus musculus

<400> SEQUENCE: 1

```
atgatccgga acgggcacgg ggctgccagc gctgctgggc tgaagggtcc gggagatcag      60
cgcatcgtgc gggtgtggtg cgatggctgg tgagtggggc gacgagggga gggcggtcac     120
ctgggcgtca cgcaccggcc gttggcggaa ccggagtctt ccgaggccgc acgaggcaac     180
ctggcctccg gtcacttagg agtgtagcgt acagacacgg gtgcatcaga cggtgcgctc     240
cccgaaaacc ggaaatgcgg ctgtctgttc gccttgggca tttacccaaa ttacctgggc     300
tggaaggctg tgagcttctc tggcaaatca gcccgtgacg tctccaagaa agtcctggag     360
ctgtcaacaa gccgaagaga taagatgttg gcctttctat aacttaccat cttcagccct     420
tcgtcgtgcc taccctggt ggatgagagg cattcggaat ggtcaccagg gctcctcagg     480
gcattcatgg cggaataggc tagactttgt gcgtttcttg tttgtctttg gttggttgct     540
gaggatggga accatagcct tgtgtgctat atatgtacag gcaagtgctc catcactgaa     600
ttacaacttc agtccccttc tgttcttttg cacctgagtc accagctttg acttcgtgtc     660
agtggactat gaccttggcc ccaccatggt gcctcaagcc cagatgcaga ctctgacctt     720
tgatctagcc ctgcctgtct agtgggcaca agggctgtcc tggaatttgc ccgttatcat     780
gtcccacctc ccaccccgtg cactgtggtg ttgacatgat gatagcccac tagggctcta     840
gaggaagcag agcagaacct atgcccagc actggcccat ggcaaagaat acaggtggtc     900
ccagggatat cccactggga tatcctcagt gtccagcata ttgctggctt ctgcatagct     960
tgaccttgac aaagtacttg tggccagacc tagatttgag gataaaagca ggtgacaggc    1020
acttgttctc tcagagagct aagccagccc tgggggtggg gaactgtcca cttgtgtcag    1080
ggtggaagta tctgctccca atgcaggact gatctcttgg ttccaagctt gagtgtggct    1140
tgttgatcca gggggactat tcttgtttag ggtgcaggag gttccatatt caaatcctag    1200
ataatctctt gtatcttgcg ggctgggagt gtagctagct cagctggtat tatgctggcc    1260
cagcatgcac aaggtcctac atttgttttg tagcacccaa cagttggctt tgggtgggaa    1320
tctcagcaga tggagtcaga agggttgaga gctgaaagtc gccgggcgtg gtggtataca    1380
cctttaatcc cagaatttgg gaggcagagg caggcagatt tctgagttca aggtcagcct    1440
ggtttacaaa gtaagttcca ggacagaaaa aaagggtca agagttgaag gtcgtcctag    1500
gttttatagt gagtttgagg ccagcctggg ctacatgaga ccttattgtc ttaaaaaaaa    1560
aaaaaagaa aaaagaaaa aagaaaaag atctgaagca gcttgaaatg cctgcccata    1620
```

```
gcaggaggca ccaacagggc aaaggcagtc taagacatgg gaaatggtta agcatctgcc    1680
agtgaacagc tgtcttggga gttcaccagc caggccttgt acctgaattt gccactcttg    1740
ctagacctgg cacccagtcc tgccctaggt ccagtactta gggtatggac aactgagaac    1800
cgacttctct gctgtaagcc caacaccggg atctgggcta ggagccctgg tgggggcctc    1860
tcagggagcc gtgctgcatc ccacacaaga ccctcagtct cctgtctgtc ctcacagcta    1920
tgacatggtg cattatggcc actccaacca gctacggcag gcacgggcca tgggggacta    1980
cctcatcgtg ggtgtgcata cggatggtaa ggtggggccc gatgtgccgg acagtccaat    2040
ggattaagcc tacagggcat ggggtggggc agaggggcgg gcagaatggt tccagcttcc    2100
ttccccagag cacagtggtg actcaggagc ttagagagt aacatagcct ggtaccagct    2160
atagagagct gtggcaacac aggacagctg tattgtctgc ccctacccg gttcttgaaa    2220 cagaagagac tgaaccctct tcttagttat ccagcagatg cccccgagca cacgccctgg    2280
ccaaaggaca atgctgttgg cacggggccc tgccttgtgg gcataccatt tgcacactgc    2340
agccttgcga cccagactcc tggacatcac ttaccttgtc ttgtccttt ctctgtccct    2400 agaggagatt gccaagcata aggggccccc ggtgtttacc caggaggaga ggtacaagat    2460
ggtacaggcc atcaagtggg tggatgaggt ggtgcccgct gctccctacg tcaccaccct    2520
ggagacactg gacaagcaca actgtgactt ctctgttcac ggcagtgagt gggcagggtc    2580
tgaggtgggg gctgggcagt cagccctgct gacctagtca cagagacagt gggcttttca    2640
tcttggctca tcctatgcac atgcaaggaa gctctgggac catccccaga gcagtggcaa    2700
agggaagggg gcccctgggg gctctcagtt aaaaatccct gtttatgcag gagagatggc    2760
tcagcagtta agagcactga tgttcttcca gaggtcctga gttcgattcc tagcaaccac    2820
atggtggctc acaaccatct gtaatgggc tccgatgcct tcttctggta tatctgaaga    2880
cagcaatggt gtacccacat acatgaaata aatgaattaa aaaaatctaa aaaaaaaaa    2940 aaatttgccg ggcgtggtag cgcatggcac tcaggaggca gaggcaggcg gatttctgag    3000
ttcaaggaca gcctggtcta caaagtgagt tccaggacag ccagggctac acagagaaac    3060
cctgtctcaa aacccaaaa aaaaaagaa gaaaaaaaa ccccccaaaaa acaaaccctg    3120 tttatgagcc tagtgtgatg acacataact atcatcttag cattagtact gaggaggctg    3180
aaacgggaca ttaagtgttc tggattagct gggcggtggt ggtgcacgcc tttagttctg    3240
gcacttggga gacagaggca ggtggatttc tgagttcaag gccagcctgg tctataaata    3300
aagtaagttc cagaacagcc aaggttaatc agagaagcct tgttccaaaa agagttccag    3360
gtcaccctgg gatacatagc aagacatgcc ctgcccccct ctcaaaataa caacaaaaca    3420
ggaacaaatc ctttctgtg tgcgtgtcac ctctagatga catcacgctg acagtagacg    3480
gccgagacac ctatgaggaa gtgaagcagg ctgggaggta caggtaggtc cagggagtgg    3540
ggctcaagag gagacccct gcctagctct ccttgttgct gtgttgacat atataccctg    3600
caaggcattt gggtcctcgg tcaggtgtgg aaagtgcagg acagcatgct ttgtgtgacc    3660
aaccccaggg cctctgcggt gctaccaggc atagctctgc cagatggcag cattctcgat    3720
catcaccgtt tgtaggacat ccttagactc gtagactcgg tagtctcagg tgcccctgga    3780
gagctgcctt tttattttaa ttaactgtaa tttaaagagc cagctgtggc cagtggttcc    3840
tatagggaca gagcagccag gaatgcatat caggggttgcc tgagtgtaat agaggccaga    3900
gggaacaacg ttggaatggg gggggccaga actggtatgt cctcaatgtg acctgcctac    3960
```

-continued

```
tccctggagt tacgttgtac agctgagtga gcccattgct cctgcccag tctggctttc    4020
tgttgtgggt gggtggtcct gggttagggt tgtgtccctc aggtggcttc tgcctatagc   4080
agagcctcag gattgtcctg gatgaaaacc tccaccttac ctctgtccca gagagtgcaa   4140
acgcacccag ggtgtgtcca ccacagacct cgtgggtcgc atgctgctgg tgaccaaggc   4200
ccatcacagc agccaggtga gtccaaacgg atgggtctg ggatacggtc cctgggctaa    4260
ggacacgggg gagggtgggt gcaggggggg gggtgcacca cctagccacc ctcaggttta   4320
tcccgtttct ctccctgacc aaccccttag tgggctccgg ggccatggcg tgctgggccc   4380
agggttggca gtcaggaggg caaggtccct tagtttcttg cccttgtgtg caggagatgt   4440
cctctgagta ccgggaatat gctgacagtt ttggaaaggt gagtacagcc tggctcgctg   4500
aggccactct ggaaatccag ttgacattcc cacccacccg ttaggcgtcc catggggaaa   4560
ggatggccca aagcttcagt gtctgccctc ctccctctct ttcccagtgc tgaccaggta   4620
ctgaccatca ggcttggcca gctagtggat gctgggaggg aggacaggca agaggtggcc   4680
agtcccagca gccacttctt ggaggaggag caaggactgc ccaccttaca ggtgggatct   4740
aaccaaatgg cctggccctc tctccctttg tagccccctc acccgacacc tgccggggac   4800
acactttcct cagaagtctc ctcccaggtg accagatggt gccctcaggg tgccgggtcc   4860
cccagagggc tgtgtctgct ggccactggg ctctgcgcct gctcctggtg gtgttgccag   4920
gcagagctgg tgttgactgc attatcttct gtggccaccg ggtggagcca cagtcctgct   4980
agctacagtg gtcctgcgtg gccttaccat ggtgtgtccc tgcccctgcc ccaagtgcct   5040
gcctggacac agcccccagc tgtgctgctg ggttattgac aggctggggt ttgggggagt   5100
ccagcctgta atgctctgtg caactcccat cacccacact tacgacaggg gcacagggag   5160
ccctgggccc agaagaatga ccaaggggag ggtactgggt gagggcaca catagaggcc    5220
tctaccactg actggttcct tctcttgact aacagtgccc tggggggcag agcccctgga   5280
cagggtgtc ccagtttcta cagacatccc agaagatcat ccagtttgct tctgggaagg    5340
agccccagcc cggggagacg gtcatctatg tggctggtgc cttgacctg ttccgtatcc    5400
tctgctgccc gaagtcatgc ctcagagtgg gacccatagc ctccaaggct ccagggttga   5460
gctgggttgt ggtgggtgcg gccttcacca gggagaatgg cacggggtcc cttgggtgcc   5520
cattgctgtt acctggcctg cttcctcct ctccatccat ggggttgggg atggagcaca    5580
gggctctgcg tatccgaggc cagtgacctc ttgctgaact acaacccaa gtcttgctct    5640
cttgagacag aattttcctg tgtagtccag gctgacctag aacttgcaat actcctgcct   5700
ccgccacgca agtgctgggt ttacaagaac accatgatac acagctagtt actgcttctt   5760
aatctggata tagacatcgg gcacgtggac ttcctacagg aggtgcacaa gctagccaag   5820
aggccctacg tcatcgccgg cctacacttt gaccaggtct ctgccctcct ccttgcttgc   5880
ttctcagcac cccgtcagct gatgggccat ggggtccctc aaggggcctt gctgggtca    5940
gtgttgggca caggtggcct ctgaaggact gaggaggctc caggtgcctg cgaaggcaag   6000
cttggctctc ttctggagtc caggacagcc ctgcctaggg tgttcctatg agaggggca    6060
cttttcccag cttctgccca cgacggccag ctgggaggga aggcaccatt catttgaggt   6120
ccccagctg agccaaactc actggccta ggaagtaaac cggtacaagg caagaacta     6180
ccccatcatg aacctgcacg agcggactct cagtgtgctg gcctgccggg taagtgaact   6240
gggagtcagg gccgggcggc tgggccctac tgggtgcagt ttcttcccc tgctgaagga    6300
gtctgagggt cccctttgcc cactggccct ggccgtgtcg ccctgccctg ctggctcccc   6360
```

```
tggcctcctc tgccacgctc tagccctcta gctcgccagg gatgaggact gagtgaggtg    6420
cttcactggc tgtgtttccg cagtatgttt cagaagtggt gattggggca ccatactccg    6480
tgacagcgga gctcctgaat cacttcaagg tgaggcttcg ctcaaagttc tcctgagcag    6540
aacatgatgc taatcttcct agaggctctt gcctgcttca gcctgggcca gttttttggg    6600
gtttgggcta gccctaagtg gttgtcagtg gtggcatagc aactctgagg aagtctcctg    6660
accttgctcc ctttccaggt ggacctggtg tgtcacggga agacagagat tgtacccgac    6720
agggatgggt ctgaccccta ccaggtgggt tgcccggcgt gggctgcctc ggggaagtag    6780
gtgcaaccat ccttcctggt attggtctcc catggggtgga gggacagctg ggggtgtctc    6840
tgtggtcagg agacctctca tctcccactt ctcttcccat tgaggcctcc aggagcccaa    6900
gagaagaggc atcttctatc agattgacag tggcagtgac ctcactacag acctgattgt    6960
gcagaggatc atcaagaaca ggtgtgtctc ctccctcc ctctgccacc ctcccccta      7020 ctgggttggc agtgggcaaa ccccagtat tggagagaac caacctacaa cccgtctggc    7080
cccaggctgg agtatgaagc acggaatcag aagaaagaag ccaaggaatt agcctttctg    7140
gaggccacga agcagcagga ggcgccgcct ggaggggaga ttgactag                 7188
```

<210> SEQ ID NO 2
<211> LENGTH: 870
<212> TYPE: DNA
<213> ORGANISM: Homo sapiens

<400> SEQUENCE: 2

```
tgagaacgga actcgggtta tttcagcccc ggcctgcaga gtggaagcgc ccagcggcct      60
ttcctcgctc accaggccag tctcagggcc tcaccgtatt tctactacta cttaatgaaa    120
aagtgtcaac tttatagaat cctctctgta ctggatgtgc ggcagagggg tggctccgag    180
cctcggctct atgcagacct tttatttct attaaacgtt tctgcactgg cttccggtgt    240
ccccgagtgg tcggcccggg ctcccgggc tcaggtctgc cgcctggcag ctcggtcgtg    300
gcttaaaact cccttggttg dacaggggac aactgtagat tattgtgcca aaaataaga    360 aaaaaaactc ccctggttgg dacagcgccc cgtggaggtt cccggaggtg gcggcggtgg    420
gacggtcccc acgccgcact gccccgccag ccgagcgcca ggtgtgggcg gtgcggagag    480
gccaggtgtg ggtcggggggg cggggctcgg aaagcgcggc acacgccatt ggctgtgcgt    540 ttggagggggg cgggactctg tcaggggctc acgccattgg ccgtgcgcgg aggtgcggtg    600
gggcgcggcc ttcgggggt ggggctcggg gcggagggcg ggaggcgggg cggggggaagc    660 gggggctggg ctcgggccga gcgccgaccc attggccgtg cgcagcgggt gaggcccgcg    720
tgacggccgc tgagcgtgcg ctggcggggc gggcggcggc gctcggagtc gccggagct    780 gccaggctgc tccgcgcgcc gctgcgggc catgatccgg aacgggcgcg gggctgcagg    840
cggcgcagag cagccgggcc cggggggcag                                    870
```

<210> SEQ ID NO 3
<211> LENGTH: 39
<212> TYPE: DNA
<213> ORGANISM: Mus musculus

<400> SEQUENCE: 3

```
tgtcagctca cacaattcca aggaaactg gccttgctg                             39
```

<210> SEQ ID NO 4

```
<211> LENGTH: 24
<212> TYPE: DNA
<213> ORGANISM: Artificial Sequence
<220> FEATURE:
<223> OTHER INFORMATION: DNA sequence

<400> SEQUENCE: 4
tgtcagctca cacaattcca aagg                                              24

<210> SEQ ID NO 5
<211> LENGTH: 24
<212> TYPE: DNA
<213> ORGANISM: Artificial Sequence
<220> FEATURE:
<223> OTHER INFORMATION: DNA sequence

<400> SEQUENCE: 5
tcagcaaggc cagtttcctt tgga                                              24

<210> SEQ ID NO 6
<211> LENGTH: 19
<212> TYPE: DNA
<213> ORGANISM: Artificial Sequence
<220> FEATURE:
<223> OTHER INFORMATION: DNA sequence

<400> SEQUENCE: 6
tctcctggct gctgtgatg                                                    19

<210> SEQ ID NO 7
<211> LENGTH: 22
<212> TYPE: DNA
<213> ORGANISM: Artificial Sequence
<220> FEATURE:
<223> OTHER INFORMATION: DNA sequence

<400> SEQUENCE: 7
ccgtgaacac agaagtcaca gt                                                22

<210> SEQ ID NO 8
<211> LENGTH: 18
<212> TYPE: DNA
<213> ORGANISM: Artificial Sequence
<220> FEATURE:
<223> OTHER INFORMATION: DNA sequence

<400> SEQUENCE: 8
cacctcgtcc acccattt                                                     18

<210> SEQ ID NO 9
<211> LENGTH: 18
<212> TYPE: DNA
<213> ORGANISM: Artificial Sequence
<220> FEATURE:
<223> OTHER INFORMATION: DNA sequence

<400> SEQUENCE: 9
ggccacgcgt cgactagt                                                     18

<210> SEQ ID NO 10
<211> LENGTH: 18
<212> TYPE: DNA
<213> ORGANISM: Artificial Sequence
<220> FEATURE:
<223> OTHER INFORMATION: DNA sequence
<220> FEATURE:
<221> NAME/KEY: modified_base
```

```
<222> LOCATION: (6)..(7)
<223> OTHER INFORMATION: modified base is i
<220> FEATURE:
<221> NAME/KEY: modified_base
<222> LOCATION: (11)..(12)
<223> OTHER INFORMATION: modified base is i
<220> FEATURE:
<221> NAME/KEY: modified_base
<222> LOCATION: (6)..(7) (11)..(12) (16)..(17)
<223> OTHER INFORMATION: modified base is i

<400> SEQUENCE: 10
acgggnnggg nngggnng                                               18

<210> SEQ ID NO 11
<211> LENGTH: 17
<212> TYPE: DNA
<213> ORGANISM: Artificial Sequence
<220> FEATURE:
<223> OTHER INFORMATION: DNA sequence

<400> SEQUENCE: 11
caggaaacag ctatgac                                                17

<210> SEQ ID NO 12
<211> LENGTH: 20
<212> TYPE: DNA
<213> ORGANISM: Artificial Sequence
<220> FEATURE:
<223> OTHER INFORMATION: DNA sequence

<400> SEQUENCE: 12
taatacgact cactataggg                                             20

<210> SEQ ID NO 13
<211> LENGTH: 20
<212> TYPE: DNA
<213> ORGANISM: Artificial Sequence
<220> FEATURE:
<223> OTHER INFORMATION: DNA sequence

<400> SEQUENCE: 13
ggatttgcgg ggggcctccg                                             20

<210> SEQ ID NO 14
<211> LENGTH: 21
<212> TYPE: DNA
<213> ORGANISM: Artificial Sequence
<220> FEATURE:
<223> OTHER INFORMATION: DNA sequence

<400> SEQUENCE: 14
acggcaggca cgggccatgg g                                           21

<210> SEQ ID NO 15
<211> LENGTH: 20
<212> TYPE: DNA
<213> ORGANISM: Artificial Sequence
<220> FEATURE:
<223> OTHER INFORMATION: DNA sequence

<400> SEQUENCE: 15
acgctgacag tagacggccg                                             20

<210> SEQ ID NO 16
<211> LENGTH: 21
<212> TYPE: DNA
```

```
<213> ORGANISM: Artificial Sequence
<220> FEATURE:
<223> OTHER INFORMATION: DNA sequence

<400> SEQUENCE: 16
ggagatgtcc tctgagtacc g                                         21

<210> SEQ ID NO 17
<211> LENGTH: 21
<212> TYPE: DNA
<213> ORGANISM: Artificial Sequence
<220> FEATURE:
<223> OTHER INFORMATION: DNA sequence

<400> SEQUENCE: 17
ttctgggaag gagccccagc c                                         21

<210> SEQ ID NO 18
<211> LENGTH: 20
<212> TYPE: DNA
<213> ORGANISM: Artificial Sequence
<220> FEATURE:
<223> OTHER INFORMATION: DNA sequence

<400> SEQUENCE: 18
accatactcc gtgacagcgg                                           20

<210> SEQ ID NO 19
<211> LENGTH: 21
<212> TYPE: DNA
<213> ORGANISM: Artificial Sequence
<220> FEATURE:
<223> OTHER INFORMATION: DNA sequence

<400> SEQUENCE: 19
gtatgcacac ccacgatgag g                                         21

<210> SEQ ID NO 20
<211> LENGTH: 21
<212> TYPE: DNA
<213> ORGANISM: Artificial Sequence
<220> FEATURE:
<223> OTHER INFORMATION: DNA sequence

<400> SEQUENCE: 20
ctcccagcct gcttcacttc c                                         21

<210> SEQ ID NO 21
<211> LENGTH: 23
<212> TYPE: DNA
<213> ORGANISM: Artificial Sequence
<220> FEATURE:
<223> OTHER INFORMATION: DNA sequence

<400> SEQUENCE: 21
ttccaaaact gtcagcatat tcc                                       23

<210> SEQ ID NO 22
<211> LENGTH: 21
<212> TYPE: DNA
<213> ORGANISM: Artificial Sequence
<220> FEATURE:
<223> OTHER INFORMATION: DNA sequence

<400> SEQUENCE: 22
ggcaccagcc acatagatga c                                         21
```

```
<210> SEQ ID NO 23
<211> LENGTH: 21
<212> TYPE: DNA
<213> ORGANISM: Artificial Sequence
<220> FEATURE:
<223> OTHER INFORMATION: DNA sequence

<400> SEQUENCE: 23
accttgaagt gattcaggag c                                      21

<210> SEQ ID NO 24
<211> LENGTH: 20
<212> TYPE: DNA
<213> ORGANISM: Artificial Sequence
<220> FEATURE:
<223> OTHER INFORMATION: DNA sequence

<400> SEQUENCE: 24
ggtgggcaca gggcaagggc                                        20
```